US009816869B2

(12) United States Patent
Denner et al.

(10) Patent No.: US 9,816,869 B2
(45) Date of Patent: Nov. 14, 2017

(54) METHOD FOR EVALUATING A MEASUREMENT RESULT OF A THERMAL ANALYSIS, AS WELL AS USE OF THE METHOD, COMPUTER UNIT, COMPUTER PROGRAM PRODUCT AND SYSTEM FOR PERFORMING THE METHOD

(71) Applicant: NETZSCH-GERÄTEBAU GMBH, Selb (DE)

(72) Inventors: Thomas Denner, Selb (DE); Juergen Blumm, Selb (DE); Otto Max Schaefer, Selb (DE); Markus Hollering, Wunsiedel (DE); Thilo Hilpert, Selb (DE); Alexander Frenzl, Schoenwald (DE); Stefan Lauterbach, Selb (DE); Andreas Strobel, Auerbach (DE); Gabriele Kaiser, Selb (DE); Stephan Knappe, Doehlau (DE); Rolf Preuss, Einbeck (DE); Michael Gebhardt, Selb (DE); Elena Moukhina, Selb (DE); Alexander Schindler, Leupoldsgruen (DE); Matthias Gradl, Sesslach (DE); Gunther Herr, Haarth (DE); André Nijmeh, Merkendorf (DE); Stefan Schmoelzer, Issigau (DE); Markus Meyer, Ehingen (DE)

(73) Assignee: Netzsch-Gerätebau GmbH, Selb (DE)

( * ) Notice: Subject to any disclaimer, the term of this patent is extended or adjusted under 35 U.S.C. 154(b) by 665 days.

(21) Appl. No.: 14/329,142

(22) Filed: Jul. 11, 2014

(65) Prior Publication Data
US 2015/0019157 A1 Jan. 15, 2015

(30) Foreign Application Priority Data

Jul. 12, 2013 (DE) .......................... 10 2013 011 730

(51) Int. Cl.
*G01K 1/00* (2006.01)
*G01K 3/00* (2006.01)
(Continued)

(52) U.S. Cl.
CPC ............... *G01K 3/10* (2013.01); *G01N 25/20* (2013.01); *G06F 17/16* (2013.01); *G06F 17/18* (2013.01)

(58) Field of Classification Search
CPC ........ G01V 9/00; G01V 99/005; G01V 9/007; G01V 11/002; G01V 8/00; G01V 8/10;
(Continued)

(56) References Cited

U.S. PATENT DOCUMENTS

2002/0085036 A1* 7/2002 Nakatani ............... G06T 11/206
715/764
2013/0336355 A1 12/2013 Neumann et al.

FOREIGN PATENT DOCUMENTS

| DE | 19825472 A1 | 1/1999 |
| DE | 102009038343 A1 | 8/2011 |
| DE | 102012105101 B3 | 7/2013 |

* cited by examiner

*Primary Examiner* — Roy Y Yi
(74) *Attorney, Agent, or Firm* — Whitmyer IP Group LLC (57) ABSTRACT

A method for evaluating a measurement result of a thermal analysis. A program-controlled computer unit is used to calculate at least one probability of the agreement of the measurement result with at least one dataset previously stored in the computer unit, wherein this calculation is based on a comparison of effect data previously extracted from a measurement curve of the thermal analysis with corresponding stored effect data of the dataset. The evaluation can advantageously include, an automatic recognition and classification of measurement curves and can be carried out in (Continued)

particular more efficiently, more economically and more quickly than previously, with at the same time a high quality of evaluation.

17 Claims, 6 Drawing Sheets

(51) Int. Cl.
*G01K 5/00* (2006.01)
*G01K 7/00* (2006.01)
*G01K 9/00* (2006.01)
*G01K 11/00* (2006.01)
*G01K 13/00* (2006.01)
*G01K 17/00* (2006.01)
*G01K 3/10* (2006.01)
*G01N 25/20* (2006.01)
*G06F 17/16* (2006.01)
*G06F 17/18* (2006.01)

(58) Field of Classification Search
CPC ..... G01D 3/022; G01J 5/0044; G01K 13/002; G01K 3/10; G06K 19/07762; G06N 99/005

See application file for complete search history.

METHOD FOR EVALUATING A MEASUREMENT RESULT OF A THERMAL ANALYSIS, AS WELL AS USE OF THE METHOD, COMPUTER UNIT, COMPUTER PROGRAM PRODUCT AND SYSTEM FOR PERFORMING THE METHOD

FIELD OF THE INVENTION

The present invention relates to the field of thermal analysis, in particular with regard to the evaluation of a measurement result of a thermal analysis.

BACKGROUND OF THE INVENTION

The term "thermal analysis" denotes here a method in which a sample, which can be of known or unknown composition or constitution, is exposed in a controlled manner to a temperature change, wherein one or more physical variables are measured simultaneously on the sample during this temperature control and are recorded as a temperature-dependent measurement signal.

At least one "measurement curve", which represents the measurement signal concerned, i.e. a quantitative representation of the physical variable concerned, as a function of the temperature-control temperature, thus results as a direct measurement result of a thermal analysis.

Types of measurements or measurement signals that can be used in thermal analysis are sufficiently known from the prior art, so that this will not be dealt with further. Merely by way of example, the so-called DCS signal (corresponding to the heat flow rate), the mass or change in mass and the length or change in length of the sample may be mentioned as possible measurement signals. Regarding the general prior art of these measurement methods, reference may be made for example to DE 198 25 472 B4, DE 10 2009 038 343 A1 and DE 10 2012 105 101 B3.

The evaluation of results of thermal analyses in the prior art takes place with a relatively low degree of automation. The user usually first has to detect and quantify, using his knowledge and experience, characteristic signal changes in the course of the measurement curve concerned that can be attributed to physical effects. As characteristic effects, signal maxima, signal minima or signal steps can occur in the measurement curve. These effects appearing in the measurement curve, which for the most part originate from conversions (e.g. phase transitions) or reactions of the sample, are often of central interest in the evaluation of the measurement. The prior art in this regard is that a user of evaluation software stipulates that measurement curve points or regions determined by the user himself, such as for example signal maxima, are to be marked and/or that curve integrals are to be calculated in these regions specified by the user.

In a subsequent interpretation of the evaluated measurement curve, the user's experience is again used in that, for example, a measurement curve obtained with a sample of unknown composition is compared with similar measurement curves from the literature or from the user's memory, for which measurement curves an interpretation already exists. The interpretation of the unknown measurement curve then takes place at best through conclusions drawn by analogy.

The evaluation of the measurement result of a thermal analysis practised in the prior art is therefore comparatively complicated, the evaluation results also being influenced to a greater or lesser extent by subjective assumptions and decisions made by the user. In the case of an integration of the thermal analysis as a measurement method in a more complex technical process (e.g. production of goods), the high time consumption on the evaluation of measurement results according to the known methods is also very disadvantageous.

SUMMARY OF THE INVENTION

It is an objective of the present invention to provide a novel and more straightforward way of evaluating a measurement result of a thermal analysis, wherein the evaluation should be able to be carried out particularly efficiently, economically and quickly with at the same time a high quality of evaluation, in order for example to open up new areas of application for thermal analysis, or to improve the practicability of the use of thermal analysis for existing areas of application.

According to a first aspect of the invention, this objective is solved by a method for evaluating a measurement result of a thermal analysis, wherein a program-controlled computer unit is used to calculate at least one probability of the agreement of the measurement result with at least one dataset previously stored in the computer unit, wherein this calculation is based on a comparison of effect data previously extracted from a measurement curve of the thermal analysis with corresponding stored effect data of the dataset.

It is advantageously possible with the invention to make available an evaluation result in a largely or completely automated manner. Here, (at least) one "agreement probability" between the measurement result concerned and a previously stored dataset, as it were representing a reference measurement result (e.g. measurement result of a thermal analysis of a known sample), is delivered as part of the evaluation.

The agreement probability is a quantitative measure of the similarity of the measurement result concerned with the dataset concerned, i.e. the (actual or notional) measurement result represented by the dataset.

The meaning of the term "similarity" can be specified as fixed for example by the employed program control (software) or can be provided in a variable manner by the user by user inputs. The same applies to the specific method for quantification of this similarity, i.e. the precise nature of the calculation of the agreement probability. The latter can for example also be specified as fixed or can be provided in a variable manner by user inputs.

The basic idea of the invention consists not in subjecting the direct measurement result of the thermal analysis, i.e. the measurement curve as such, to a comparison with known measurement curves, but rather to subject "effect data previously extracted from the measurement curve" to a comparison with corresponding stored effect data.

"Effect data" in the sense of the invention are a quantitative description of the initially mentioned, characteristic and locally (i.e. in relatively limited temperature ranges) occurring signal changes that arise in the thermal analysis.

The method according to the invention can thus be referred to as an "effect-based" evaluation method, from which a large number of advantages arise in particular for the application to measurement results of the thermal analysis. The fact that the method is effect-based advantageously enables a high degree of automation in the evaluation of such measurement results.

The reduction of a measurement curve to its effects (and as the case may be "effect features" described below) thus leads to high degree of efficiency and rapidity of the method. In practice, this enables the calculation of a large number of agreement probabilities between an unknown measurement curve and the known measurement curves, stored for example in a database in the form of datasets, virtually in real-time, i.e. essentially while the thermal analysis concerned is still taking place.

The effect-based comparison, implying a restriction of the temperature range (the effect) of the unknown measurement curve to be considered in an effect comparison, enables a high-quality interpretation of the individual effect concerned, independently of the remaining course of the measurement curve or the other effects present therein.

The effect-based and, as the case may be, feature-based method does not necessarily require the "measurement curve" (raw signal) in question as input variables. In principle, it is sufficient to know the mentioned effects and, as the case may be, their features as the measurement result to be evaluated. Datasets, which are based solely on literature information or literature values of effects, can thus advantageously also be stored in the computer unit.

In an embodiment, the effect data relate to a DSC signal, i.e. can be regarded as a quantitative description of the locally occurring characteristic changes in the DSC signal. Alternatively, the evaluation of another physical variable measured on the sample, in particular for example mass or change in mass or length or change in length, can take place. In a development, provision can even be made such that the effect data represent a quantitative description of the effects of measurement curves of a plurality of (different) physical variables.

In a preferred embodiment of the invention, the effect data at least take account of minima, maxima and steps in the course of the measurement curve. Furthermore, kinks in the course of the measurement curve are also taken into account in a development.

Furthermore, in another development, maxima, minima and steps in the course of the derivative of the course of the measurement curve are taken into account.

The computer unit preferably comprises a memory unit, in which a large number (e.g. more than 20, in particular more than 100) datasets of effect data are stored for given known materials or samples. The number of stored datasets can expediently be provided in a variable manner, for example by corresponding user inputs to add or delete individual datasets. In particular, an addition of datasets in a database of the computer unit can take place, said datasets being generated on the basis of an extraction of the required effect data from a measurement curve which has been recorded by a thermal analysis of a sample of known composition.

The comparison of the effect data, on the one hand extracted from the measurement curve concerned and on the other hand defined by the dataset concerned, delivers as a result a measure of the similarity or the agreement probability of effects and thus ultimately of the measurement curves concerned (on the one hand unknown measurement curves and on the other hand actual or notional measurement curves represented by the datasets).

To carry out the comparison, advantageous use can in principle be made of algorithms which are known as such from the prior art, for example numerical or analytical algorithms, or also statistical algorithms. Suitable numerical algorithms can be based for example on neuronal networks or fuzzy logic. Statistical algorithms can for example work according to the maximum likelihood principle.

As already mentioned, such algorithms can, within the scope of the invention, be specified as fixed or can also be provided by user inputs in a variable manner structurally and/or only in individual parameters (e.g. thresholds etc.).

By means of the effect-based and, as the case may be, feature-based character of the evaluation method according to the invention, the mentioned comparison algorithms known per se can, within the scope of the invention, advantageously thus be combined, for example, with the knowledge and assumptions of the user, the latter specifying by a user input in the evaluation whether the measurement result to be evaluated relates to a pure-substance measurement curve or a multi-component measurement curve. In the latter case, the measurement curve of the thermal analysis emerges as a superposition of underlying pure-substance measurement curves. The corresponding user input can thus be used advantageously to adapt the employed comparison algorithm. When use is made of a multi-component algorithm, the calculated agreement probabilities are for example in a relationship with the quantity-related proportions of the pure substances.

A further advantage of the invention of great importance in the practice of thermal analysis consists in the fact that the employed comparison algorithm can be constituted in a straightforward manner, so that different mathematical weights and therefore varying degrees of importance can be assigned to different effect types and/or their effect features. These different mathematical weights can be specified as fixed or can be specified in a variable manner by user inputs. The importance of the "similarity" of compared measurement curves or effect data with one another can thus be advantageously controlled.

Variable parameters of the algorithm arising from user inputs allow the evaluation method to be adapted in the optimum manner to different tasks by the fact that different sets of parameters are used for different tasks.

For example, in the case of the evaluation of measurement results on (partially) crystalline samples, a greater weight can be assigned to endothermic melting effects than to glass transitions, since partially crystalline samples in particular display melting effects. In contrast with this, in the case, for example, of amorphous, i.e. non-crystalline, samples, the glass transitions can be given mathematically greater weight than the melting effects.

In the case of a variability of the mentioned parameters of the algorithm, the advantage also arises that the evaluation method can be used as a definable database search. The parameters of the algorithm can be perceived as filter criteria, as a result of which the measurement curves defined by the datasets can be classified in a database in a targeted manner according to the filter criteria.

For example, all the properties of a melting effect which becomes apparent in a DSC measurement curve by a local maximum (with a corresponding definition of the DSC signal, i.e. with "exotherm downwards"), could be classified as unimportant, apart from the area (curve integral) of the corresponding "melting peak", which reflects the melting enthalpy. In this case, the measurement curves represented by the datasets in a database can be arranged for example classified according to the magnitude of their melting enthalpy.

The mentioned parameters of the algorithm or algorithms used in the comparison can, as mentioned, be provided in a variable manner by the user. Alternatively or in addition, such a parameter change can also be provided in a self-learning manner. The latter is understood to mean that the parameters change for example independently (controlled solely by employed software), for example taking account of the datasets stored in the computer unit. Moreover, interactions by the user can however also lead to the indirect changing of parameters. Interaction means here the rendering of a judgement regarding the similarity of the measurement curve concerned with a stored measurement curve or the active assignment (executed by the user) of a measurement curve to be evaluated to one of preferably a plurality of previously defined classes of datasets in the computer unit.

In an embodiment of the invention, provision is made such that the effect data for each effect are represented as a given feature vector, the vector components whereof represent quantitatively specific properties of the effect concerned.

A plurality of different effect types are preferably taken into account, wherein the feature vectors of different effect types expediently quantify different "specific properties" (according to the effect type).

In particular, one or more or all of the following properties can for example be used here as vector components for the effect type "maximum" and the effect type "minimum": area (curve integral), temperature of the maximum and minimum in the narrower sense (i.e. temperature at which the signal value concerned is at a maximum or minimum), start temperature, end temperature.

In particular, one or more or all of the following properties can for example be used as vector components in the case of the "step" effect type: start temperature, average temperature, end temperature, step height.

It goes without saying that a "step" in the course of a measurement curve usually involves a constant signal change, so that the effect denoted by this term within the scope of the invention has, unlike in the strictly mathematical sense, a more or less large width. The mentioned properties "start temperature" and "end temperature" as features of the signal steps take account of this fact.

With regard to the aforementioned properties "start temperature" and "end temperature", it should be noted that these temperatures can be defined in different ways. In this regard, provision is made according to an embodiment such that, for at least one effect type, a characterisation takes place by at least two (differently defined) start temperatures and/or two (differently defined) end temperatures. This possibility will be dealt with in greater detail below by reference to an example of embodiment.

In an advantageous development of the evaluation method, the latter also comprises the step of an extraction of the effect data from the measurement curve of the thermal analysis by using the computer unit.

As a result of this development, the evaluation method becomes suitable for processing the direct measurement results of the thermal analysis, i.e. the "measurement curve" itself, as an input variable. To this extent, this development is of interest especially with the implementation of the evaluation method in or in connection with a device for performing the thermal analysis.

According to a further aspect of the invention, therefore, a system is provided which comprises both a device for performing a thermal analysis as well as a computer unit, which is designed for the evaluation of a measurement result of the thermal analysis.

In particular, the system can for example represent a device for performing the thermal analysis which is modified in such a way that a program-controlled computer unit of the device, which is in any case used for the performance (operational control) of the thermal analysis (in particular control of the sample temperature control), is additionally used to perform the evaluation method according to the invention.

The performance of the extraction of the effect data from the measurement curve can take place in two sub-steps, preferably employing the computer unit in each case, wherein a "segmentation of the measurement curve" takes place in a first sub-step and the "evaluation of the effects" (feature extraction) takes place in a second sub-step on the basis of the previously obtained segments of the measurement curve.

The sub-step "segmentation of the measurement curve" means that the measurement curve is split up into meaningful regions for further evaluation, i.e. into regions in which an effect is present in each case, and into regions in which no effect is present. The regions are defined here by a given temperature range. In other words, in this sub-step the given effects in the measurement curve are identified and demarcated from one another, for example by means of a special segmentation algorithm running on the computer unit.

The function of the employed segmentation algorithm can for example be based on taking account of predetermined threshold values of the measurement signal. Through detection of threshold values of the measurement signal being exceeded or fallen below, the effect types "maximum" and "minimum" can in particular easily be detected and quantified in their temperature-related expansion (e.g. on the basis of the start temperature and end temperature).

Provision is made in an embodiment such that a "relatively low-lying" start temperature and a "relatively high-lying" end temperature is calculated for each effect by means of the step "segmentation of the measurement curve", wherein the region from the start temperature to the end temperature defines the region of the measurement curve in which an effect is present, i.e. is "identified". In a development, in the mentioned second sub-step "evaluation of the effects", the calculation of a further "higher-lying" start temperature and a further "lower-lying" end temperature takes place, the latter then being able in the second sub-step to enter as vector components into a respective "feature vector". This does not rule out the first-mentioned start and end temperatures (which define a larger temperature range) being used, alternatively or in addition, as components of such a feature vector.

As an alternative to or in addition to the use of threshold values for the measurement signal, threshold values can also be used for the derivative (differential quotient) of the measurement signal. The use of this criterion may be advantageous, for example in a redundant manner, also for the identification or precise quantification of maxima and minima. Moreover, this criterion is however very advantageous above all for the identification of the effect type "step". This is because it is characteristic of a step that, in the course of the temperature change, the derivative of the measurement signal first changes notably in one direction (positive or negative sign), and then, after passing through a point of inflection, changes in notably in the opposite direction. Both characteristics can easily be detected for example by an evaluation (e.g. in respect of a threshold value being exceeded) of the first derivative of the measurement signal and/or of the second derivative of the measurement signal. A step height can be detected and quantified by jointly taking into account the difference between the measurement signal values on the one hand at the start and on the other hand at the end of the step.

The effect type "kink", which could also be referred to as "knee", is characterised by a notable, more or less abrupt change in the first derivative of the measurement signal at the point concerned in the course of the measurement signal. This is equivalent to a more or less pronounced extremum of the second derivative of the measurement signal at this point.

To this extent, the evaluation of the first and/or the second derivative of the measurement signal can in particular also be used very advantageously for the identification of effects of the type "kink" or "knee" as part of the segmentation algorithm.

The second sub-step "evaluation of the effects" (extraction of the features) can also be carried out partially or completely automated by means of an extraction algorithm running on the computer unit. In this sub-step, the effects identified in the preceding sub-step and demarcated on the basis of their respective temperature ranges are evaluated in respect of their (more precise) "properties" and "features" are formed by the quantification of these properties. In other words, the effect data are generated (calculated) by this sub-step. These features thus obtained can then form vector components of the already mentioned feature vector.

In a software-related variant of embodiment, provision is made such that, as a further vector component of the feature vector, a value is provided which characterises or encodes the effect type to which this feature vector relates. For example, one of the values 1, 2 and 3 could for example be assigned as the first vector component in each case, in order thereby to encode the effect types maximum, minimum and step corresponding to the value. In an alternative embodiment, the effect type is not taken into account as a specially provided vector component of the feature vector, but rather by a kind of "characterisation" of the feature vector concerned, said characterisation being implemented in some other way by the software. Finally, it is also possible to take account of the effect type of the individual feature vectors by the fact that the feature vectors for the different effect types are stored in correspondingly different areas (e.g. memory area) of the computer unit.

The "properties" considered in this second sub-step may, as already mentioned, depend on the effect type concerned. In this regard, reference is made to the explanations already provided above. In particular, the area (curve integral) can for example represent an important property to be taken into account for the effect type "maximum" or "minimum", wherein the value of the area then forms the corresponding feature of this property. For the effect type "step", on the other hand, the step height in particular is for example an important property to be taken into account. The value of this step height is then the corresponding feature which enters as a component into the feature vector for the effect concerned.

The two sub-steps of the step "extraction of effect data" explained above can each be carried out semi-automatically, i.e. software-supported, or fully automatically, i.e. completely by means of software. The effect features, which generally describe in particular the temperature-related position, the magnitude and the form of the effects concerned, are preferably placed in their own feature vector for each individual effect.

The step "extraction of effect data" has been described above as being composed of the two sub-steps "segmentation of the measurement curve" and "evaluation of the effects" (feature extraction). In a simplified embodiment of the evaluation method, the extraction of the effect data is carried out in a cruder manner just by the step "segmentation of the measurement curve". The effect data thus obtained then indicate, for each effect, at least (or only) the effect type and a temperature-related expansion of the effect (e.g. defined by a start temperature and an end temperature). The effect data then indicate, as it were, essentially only the presence of an effect (together with an effect type) at specific points of the measurement curve. The addition of the described second sub-step, with which additional features of the individual effects are quantified and taken into account in the effect data (e.g. through at least one further start temperature, a further end temperature, a mean temperature, and/or one or more curve integrals etc.), is however generally preferred and more advantageous.

In an embodiment of the step "extraction of the effect data", maxima, minima and steps in the course of the measurement curve are in particular sought and detected by the algorithm concerned. Optionally, the algorithm can for example be designed to detect maxima, minima and steps in the course of the derivative of the measurement signal.

In a development of the invention, which is also particularly advantageous especially in an integration of the computer unit in a system or in a device for performing the thermal analysis, the evaluation method further comprises the step of a "preliminary processing of the measurement curve" using the computer unit, before the extraction of the effect data described above takes place.

The term "preliminary processing of the measurement curve" is intended to signify that the measurement curve emerging directly from the thermal analysis is first subjected to one or more of the following processing steps: smoothing (e.g. by the formation of a sliding mean value), filtering (e.g. with respect to specific "frequency components" in the temperature range), elimination of specific (unimportant) regions (e.g. at the start and/or at the end of the total measurement range, in order to provide a defined start temperature and end temperature for the measurement curve subsequently to be evaluated), subtraction of an "empty curve" of the device in question for the thermal analysis (the term "empty curve" denotes here the course of the measurement signal concerned when the device for the thermal analysis is operated without a sample inserted therein), standardisation to uniform measurement conditions (e.g. in respect of a uniform sample mass or uniform heating rate, wherein this standardisation can be achieved for example by means of a mathematical standardisation algorithm obtained on the basis of a suitable physical model).

In a further development of the evaluation method, the latter also comprises the step of an assignment of the measurement result to a previously defined class of datasets using the computer unit, wherein this assignment is based on the result of the calculation of one or more agreement probabilities. In an alternative embodiment, a plurality of such classes is previously defined for the datasets, so that an assignment of the measurement result to one of this plurality of previously defined classes can take place in this step.

Such a class assignment is particularly advantageous, for example, if the evaluation is carried out in a system of the type described above, i.e. directly in connection with the thermal analysis itself. Thermal analyses carried out by means of the system can then be evaluated quickly and by means of the system to establish whether the measured samples meet or not the criteria of the specific classes.

Such classes can for example be quality classes, i.e. relating to a quality of the measured sample defined by the user. Classes such as "high quality", "average quality" and "low quality" could for example be provided for this. Alternatively or in addition, one or more other classes can also be defined in advance, e.g. material classes such as "polymer of type X", polymer of type Y" etc. Further examples of material classes are for example "thermoplastics" or "elastomers".

In this connection, provision is made according to a further aspect of the invention, for example, for the use of an evaluation method of the described type in the area of quality assurance in the production or processing of goods. In the case of a use of this kind, the following steps in particular can be provided: performance of a thermal analysis on produced or processed goods at least on a random sample basis and evaluation of the measurement results of the thermal analysis by means of a method of the described type, in particular wherein an assignment of a given measurement result takes place to one of a plurality of classes, e.g. quality classes or material classes.

In a development of this use of the evaluation method, provision is made such that, depending on the result of the evaluation, it is possible to intervene automatically (initiated by the computer unit) into the process concerned (production or processing). This intervention can for example be a controlled change in the mode of operation (e.g. operating parameters) of at least one machine used in the process (as far as, for example, stopping the machine). Alternatively or in addition, the intervention can consist in the fact that specific produced or processed goods are "removed" as rejects from the process.

BRIEF DESCRIPTION OF THE DRAWINGS

The invention will be described further below with the aid of examples of embodiment making reference to the appended drawings. In the figures.

DETAILED DESCRIPTION OF THE INVENTION

Figure 1:
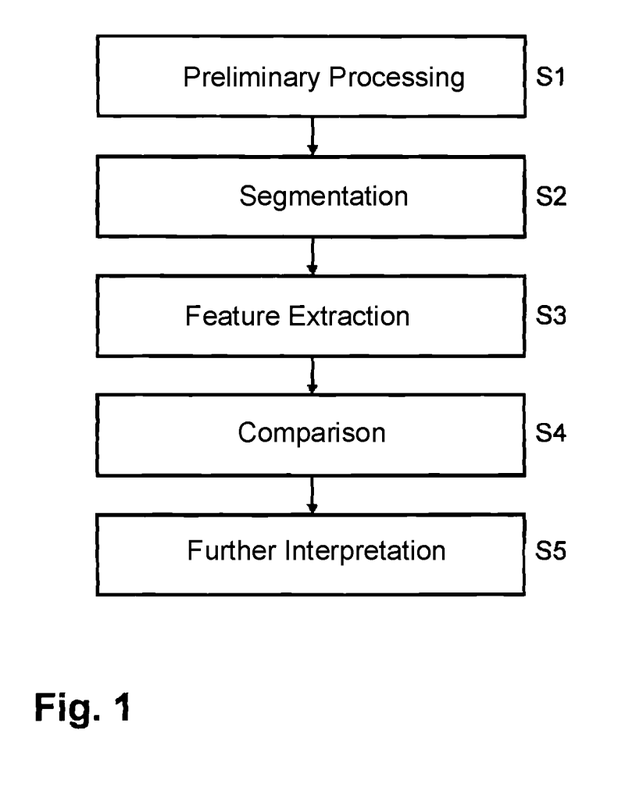
FIG. 1 shows a flow chart of a method for the automatic recognition and classification of measurement curves, which have been obtained by thermal analysis of samples.

FIG. 1 shows a flow chart of an evaluation method according to a first embodiment.

The method represented in FIG. 1 for the evaluation of a measurement result of a thermal analysis comprises steps S1 to S5 described in detail below by way of example, which can take place for example fully automatically (by means of a computer unit), or at least partially automated, while a thermal analysis measurement is still going on or after the end thereof.

Figure 2:
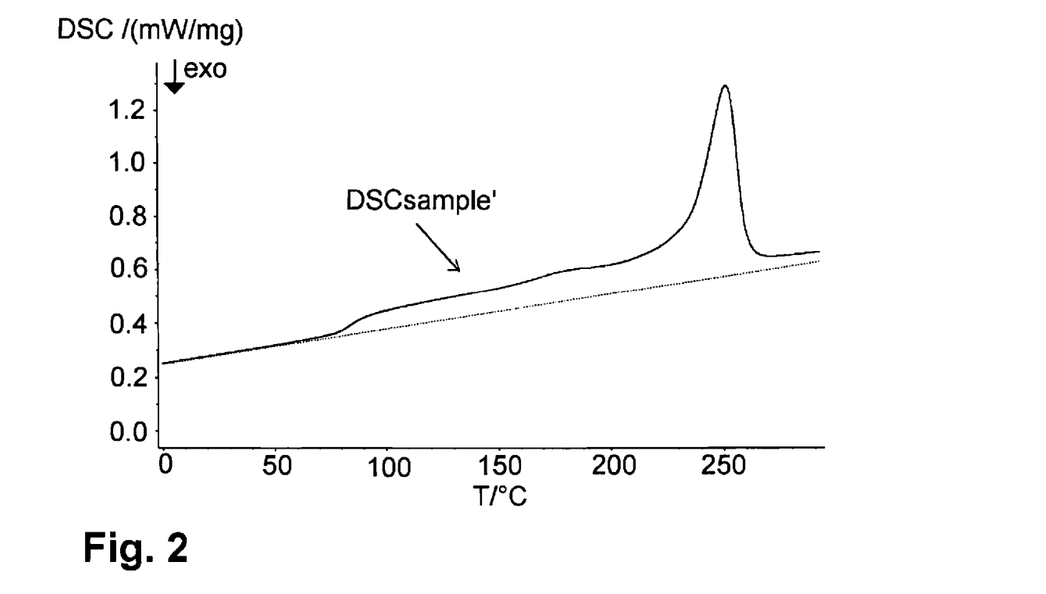
FIG. 2 shows an exemplary measurement curve obtained as a direct measurement result of a thermal analysis.

FIG. 2 shows an exemplary DCSsample' measurement curve obtained as a direct measurement result of a thermal analysis of a sample of unknown composition. The example represented is a so-called DCS' (differential scanning calorimetry) signal which is dependent on a temperature-control temperature T.

As can be seen from FIG. 2, the DSCsample' measurement curve was obtained in the course of the heating-up of the sample from approx. 0° C. to approx. 300° C. The DSCsample' measurement curve in the example comprises a fairly large number N of measurement points (e.g.: N>100), i.e. value pairs comprising temperatures T(i) and associated signal values DSC'(i), wherein i=1, 2, 3, . . . N.

With regard to FIG. 1, preliminary processing of the DSCsample' measurement curve first takes place in step S1.

The preliminary processing can comprise in particular the subtraction of the so-called empty curve of the measuring device, but alternatively or in addition also for example smoothing, averaging or filtering of the measurement curve, the omission of unimportant regions or a mathematical standardisation of the measurement curve to uniform measurement conditions (e.g. in respect of sample mass and/or heating rate).

Apart from the "untreated" (directly obtained) DSC-sample' measurement curve (continuous line), the empty curve of the analysis device concerned is also plotted with a dashed line in FIG. 2.

Figure 3:
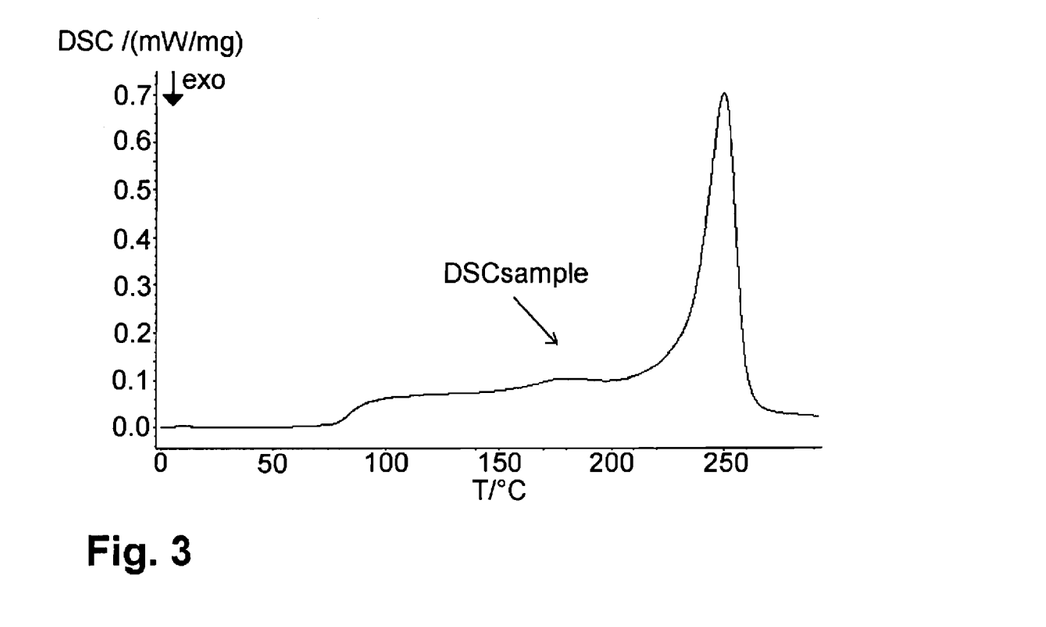
FIG. 3 shows the measurement curve that results after preliminary processing of the measurement curve from FIG. 2.

FIG. 3 shows a corrected DSCsample measurement curve, which results after preliminary processing of the DSC-sample' measurement curve from FIG. 2. This preliminary processing (step S1) comprises here the subtraction of the empty curve (dashed line in FIG. 2) from the original DSCsample measurement curve (continuous line in FIG. 2).

With regard to FIG. 1, a segmentation of the DSCsample measurement curve then takes place in step S2.

Segmentation means the splitting-up of the measurement curve into meaningful regions for the subsequent processing. This means that characteristic signal changes attributable to physical effects in the course of the DSCsample measurement curve are detected or identified at least with regard to their temperature-related position and their "type".

Quite generally, local maxima, minima or steps in the signal concerned, here of the DSC(T) signal, can in particular occur, for example, as characteristic effects in the measurement curve. These effects appearing in the DSCsample measurement curve are based on phase transitions or other endothermic or exothermic processes in the investigated sample. These effects in the DSCsample measurement curve are identified and demarcated from one another by means of a suitable segmentation algorithm running on the computer unit. This can take place in a straightforward manner, for example by taking account of threshold values of the changes in the measurement signal and the changes in the derivative DSCsample(T)/dT of the DSCsample(T) measurement signal.

Figure 4:
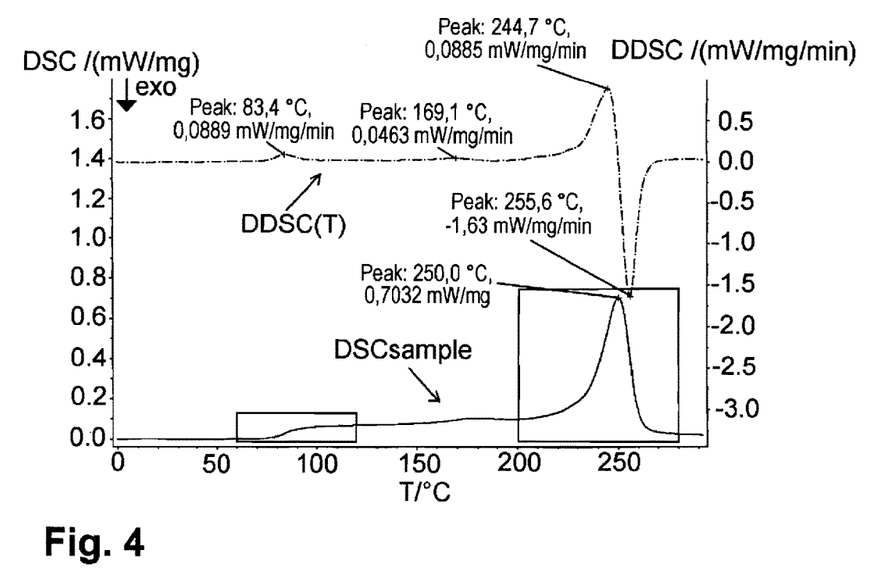
FIG. 4 shows a representation to explain a segmentation of the measurement curve from FIG. 3 for the purpose of identifying effects contained therein.

FIG. 4 illustrates the performance and the result of the segmentation (step S2) of the DSCsample measurement curve from FIG. 3 for the purpose of identifying effects contained therein.

In the example described here (FIG. 4), a (local) maximum in the DSC(T) signal for example is detected at approx. 250° C. Maxima are characterised in that a minimum and a maximum in the derivative DDSC(T) (=DSC(T)/dT; dashed line in FIG. 4) is located before and respectively after said maxima.

In the example represented, the maximum and the minimum of the DDSC(T) derivative arise approximately at T=245° C. (maximum) and respectively T=256° C. (minimum).

The temperature range of the entire effect, here of the effect type "maximum", i.e. originating from an endothermic effect in the sample (e.g. due to melting) is highlighted in FIG. 4 by a rectangle. This temperature range (temperature-related expansion of the effect) can be established for example on the basis of the DDSC(T) derivative.

As a start of the effect, a temperature could for example be established at which the amount (absolute value) of the DDSC(T) derivative exceeds a threshold value predetermined by means of the algorithm employed.

A mean temperature ("peak") of the effect can then be determined (or preferably in step S3 described below) by means of the employed algorithm on the basis of the maximum of the DSC(T) measurement signal.

An end of the effect can finally be established for example at the temperature at which the amount of the DDSC(T) derivative falls below a threshold value predetermined by means of the algorithm employed.

In the example described here (FIG. 4), moreover, an effect of the type "step" is detected approximately at T=83° C. With this kind of effect, a maximum occurs in the DDSC(T) derivative, so that this can also be detected in a straightforward manner by means of the segmentation algorithm. A step in the DCS signal can originate for example from a so-called glass transition in the material of the sample.

The temperature range of this effect can again be defined by means of a threshold value for the DDSC(T) derivative.

The significance or detection sensitivity for the aforementioned effect types can be defined for example by the fact that the absolute values of the maxima in the DSC(T) signal and the DDSC(T) derivative must exceed specific threshold values. For example, the maximum in the DDSC(T) derivative approximately at T=169° C., which can also be seen in the DSCsample measurement curve from FIG. 4, is too small for the conclusion to be drawn that there is a significant effect. The segmentation algorithm does not therefore identify any effect at this point.

With regard to FIG. 1, an evaluation of the effects (feature extraction) then takes place in step S3, whereby the effects found in step S2 are further evaluated with regard to their properties and features with the aid of the evaluation software or an extraction algorithm.

In step S3, the determination of a further start temperature and a further end temperature can in particular be carried out, for example, for each of the effects or at least the effects of at least one specific effect type. This determination can be carried out for example according to known standards such as for example DIN 51007 or ASTM E 53765, in order to determine a (further) start temperature usually referred to as "onset" and/or a (further) end temperature usually referred to as "end". These temperature values can then enter as corresponding vector components into the respective feature vector. Their calculation can be based in particular on the use of a tangent method (see for example the methods provided for this in the aforementioned standards).

Furthermore, the aforementioned evaluations in respect of a mean temperature ("peak") and/or (at least for maxima and minima) of one or more curve integrals can be provided in step S3. For the calculation of a curve integral (e.g. area beneath a maximum or minimum), one of the mentioned start temperatures and one of the mentioned end temperatures can for example be used as range limits for the integration.

Steps S2 and S3 can take place semi-automatically, i.e. software-supported, or fully automatically, i.e. completely by means of software. The effect features, which generally relate to the position, the size and the form of the previously identified effects, are placed for each existing effect in each case in a feature vector.

Figure 5:
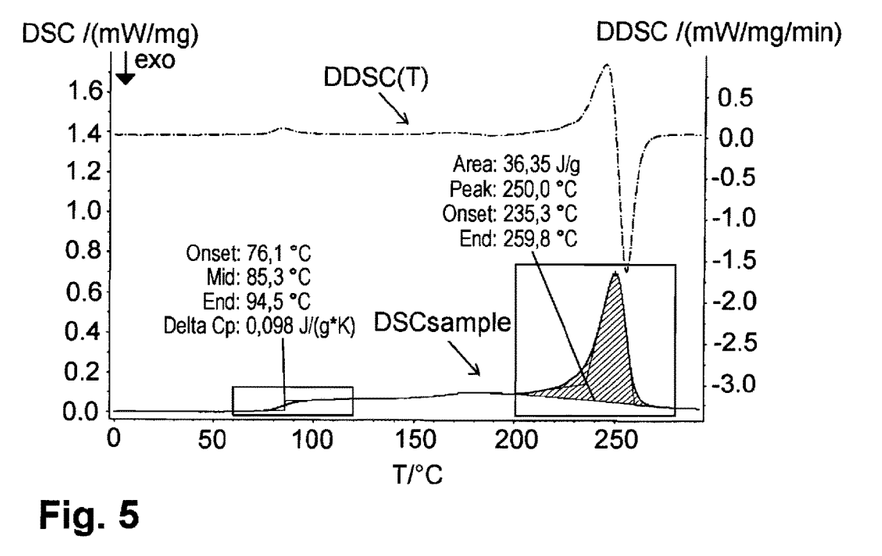
FIG. 5 shows a representation to explain an extraction of features, i.e. quantified properties of the effects previously identified in the measurement curve from FIG. 3.

FIG. 5 is a representation according to FIG. 4, wherein the properties of the effects identified in the DSCsample measurement curve that are quantified in this example are however indicated to explain the extraction of features (step S3).

In the example according to FIG. 5, the evaluation of the effects has been carried out according to known standards such as DIN 51007 or ASTM E 53765.

The features for the glass transition approximately at T=85° C. are here the extrapolated variables "onset" (start temperature), "mid" (midpoint temperature), "end" (end temperature), "delta Cp" (step height).

The properties "onset" and "end", as well as the properties "peak" (temperature of the maximum) and "area" (area) were also evaluated for the "endothermic peak" (maximum) approximately at T=250° C.

The numerical values indicated in FIG. 5 for these properties are the "features" of the given effect and form, as "effect data", components of a "feature vector" made available by the extraction algorithm for each effect as a result of step S3.

With regard to FIG. 1, there then takes place in step S4 a comparison of the effects which have been found in the DSCsample measurement curve (step S2) and more precisely quantified (step S3) with the effects which have previously been stored for "stored measurement results" in the form of datasets in a database of the computer unit used.

Figure 6:
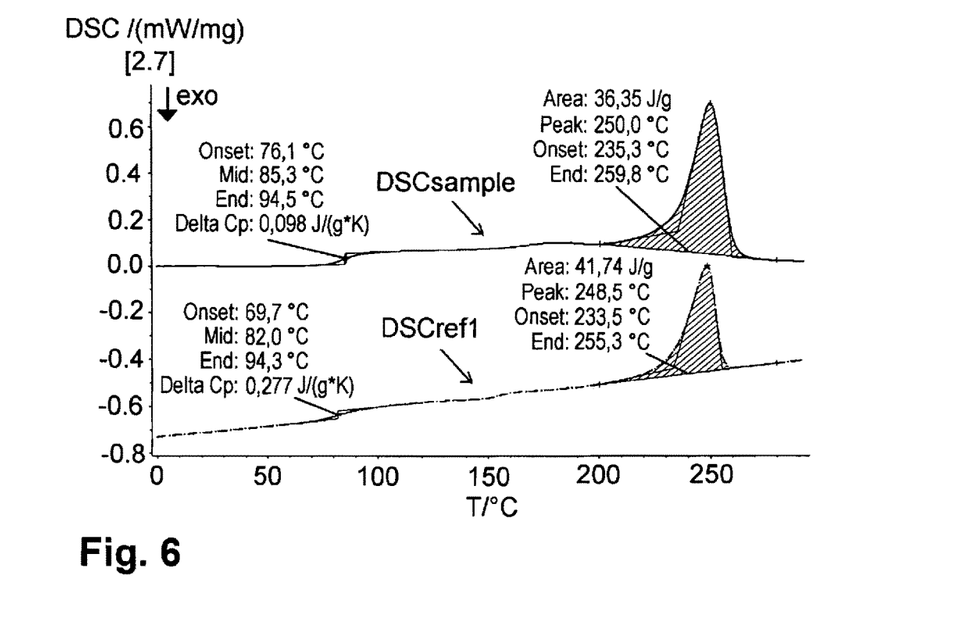
FIG. 6 shows a representation to explain the performance of a comparison between the effect data extracted from the measurement curve with corresponding effect data previously stored in a computer unit.

FIG. 6 illustrates the performance of such a comparison between the effect data extracted from the DSCsample measurement curve with corresponding effect data of an actual (previously measured) or notional (e.g. modelled from literature values for effects) measurement curve DSCref1 previously stored in the computer unit.

Measurement curve DSCref1 shown by a dashed line in FIG. 6 is an existing known curve from a database, in which a plurality of such known curves DSCref1, DSCref2, DSCref3, . . . are stored.

The above list "DSCref1, DSCref2, DSCref3, . . . " is intended to express the fact that a large number of such curves can be previously stored in the computer unit, for example more than 20 or more than 100. In this regard, it should again be noted that the number of such previously stored known curves, or more precisely the effect data corresponding to such curves, can be provided in a variable manner also for operational purposes.

Step S4 delivers as a result a measure of the similarity or agreement probability of effects and ultimately of the measurement curves in question (here, unknown measurement curve DSCsample vs. measurement curve DSCref1 from the database of the computer unit). The variables similarity and agreement probability between measurement curves are complementary to the difference between the measurement curves.

For the purpose of calculation, the (calculated) feature vectors generated in step S3 are used as input variables for a comparison algorithm of the evaluation software. The comparison algorithm can work for example according to a numerical or analytical algorithm, or also according to a statistical algorithm. An agreement probability p can for example be expressed as follows:

$$p = fp(\text{position}) \times fg(\text{size}) \times ff(\text{form}),$$

wherein fp, fg and ff represent agreement probabilities in respect of position, size and form of the effects, and wherein the corresponding effect features determined in step S4 from the measurement curve DSCample and the effect data stored for the reference curve DSCref1 are used for the calculation of fp, fg and ff.

Similar curves can thus be found through high agreement probability, as illustrated in FIG. 6. The reference measurement curve DSCref1 plotted by way of example in FIG. 6 has a high agreement probability with the unknown curve DSCsample.

Through such comparisons of measurement curve DSCsample with each of the previously stored reference measurement curves DSCref1, DSCref2, DSCref3, . . . , the unknown curve DSCsample or the underlying sample can thus be identified and/or characterised and/or classified.

Figure 9:
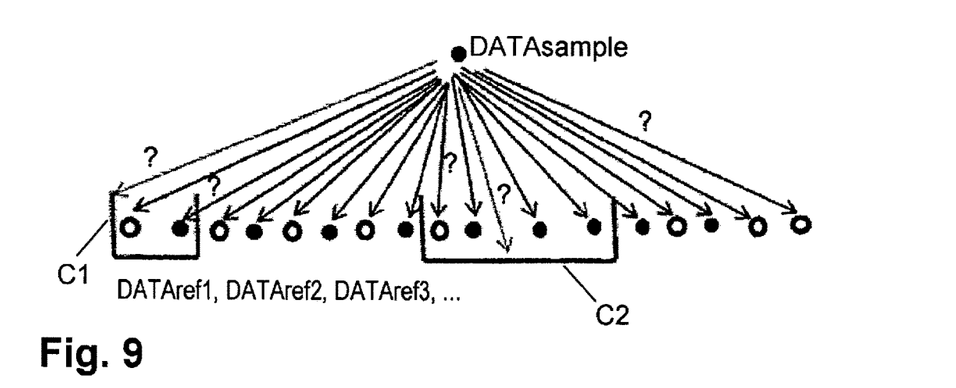
Figure 10:
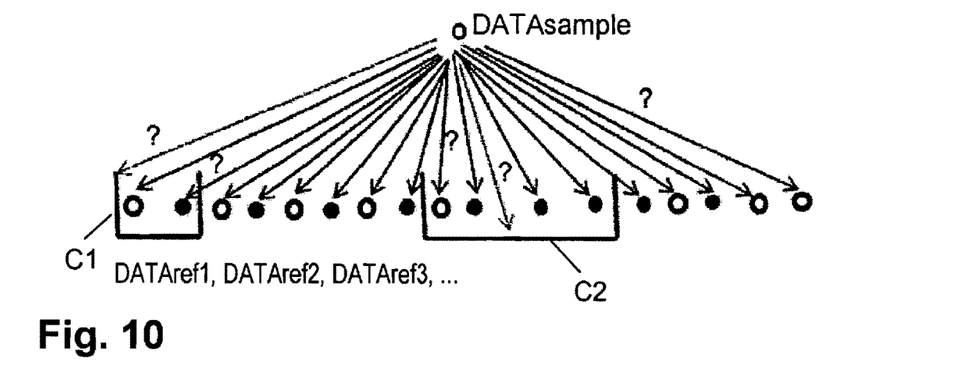

With regard to the possibility of a "classification" of the underlying sample, i.e. an assignment of the measurement result concerned to one of one or more previously defined classes (e.g. quality classes, material classes, etc.), reference is made to the explanations already provided above (and to the following explanation with reference to FIGS. 9 and 10).

If, for example, it is known that the similar measurement curve DSCref1 from the database is a measurement on a specific polymer "X", the unknown measurement curve DSCsample will have also been measured with a high probability on polymer X. With a high degree of probability, the unknown sample substance is therefore polymer X.

Finally, in the example represented, a step S5 is also provided, in which a further interpretation of the result from step S4 is carried out.

Here, further interpretations can be derived from the effects ascertained after performing steps S1 to S4, their features and the calculated agreement probabilities (similarities or differences). Qualitative and also quantitative differences from the stored curves compared to curves DSCref1, DSCref2, DSCref3, . . . , which can also be used to calculate new variables, can be used as decision criteria for evaluating an unknown measurement curve, such as for example the represented DSCsample curve.

If the described evaluation method is used for example as a measurement method in the area of quality assurance in the production of goods, decisions regarding the process of the quality assurance or the production of the goods can in turn be derived from the results of step S4, and as the case may be step S5 (see also in this regard the explanation given below).

In the example according to FIG. 5, an area of the endothermic "melting peak" of approx. 36 J/g has for example been calculated by means of the evaluation software. This value corresponds to the melting enthalpy of the sample. It can be seen from the literature or from a database curve that the identified polymer "X" has a maximum melting enthalpy of 100 J/g with full crystallinity. Accordingly, the degree of crystallinity of the unknown sample can be calculated for example by means of the further interpretation according to step S5 at 36 J/g:100 J/g=0.36=36%.

Furthermore, within the scope of the invention, new measurement curves can be added to the databases of the known measurement curves. No knowledge about the measurement curve, but only a designator or name for the measurement curve is required for this purpose.

In an embodiment, the evaluation method described above is carried out at least with steps S1 to S4 in a system which comprises both a device for performing a thermal analysis and a computer unit which is designed for the evaluation of a measurement result of the thermal analysis. The same or another program-controlled computer unit can be used to control the operation of the device for performing the thermal analysis.

Various variants of a comparison between an unknown measurement result with a plurality of known measurement results stored in a database are again explained below by reference to FIGS. 7 to 10.

The effect-based and feature-based evaluation method according to the invention (see for example the example of embodiment according to FIGS. 1 to 6) does not necessarily require as input variables measurement curves in the original sense, i.e. raw signals, such as result directly from a thermal analysis. On the contrary, the effect data extracted from a measurement curve of the thermal analysis suffice as input variables, wherein both data extracted from an actual (measured) measurement result and also data based for example solely on literature values of effects fall under the term "effect data". In the latter case, one can also speak of effect data which have previously been extracted from a "virtual measurement curve".

In FIGS. 7 to 10, the effect data based on an "actual" measurement are symbolised in each case by a "dot", and the effect data actually generated in another way (e.g. from literature data or from a "virtual measurement curve") are in each case symbolised by a "circle".

Figure 7:
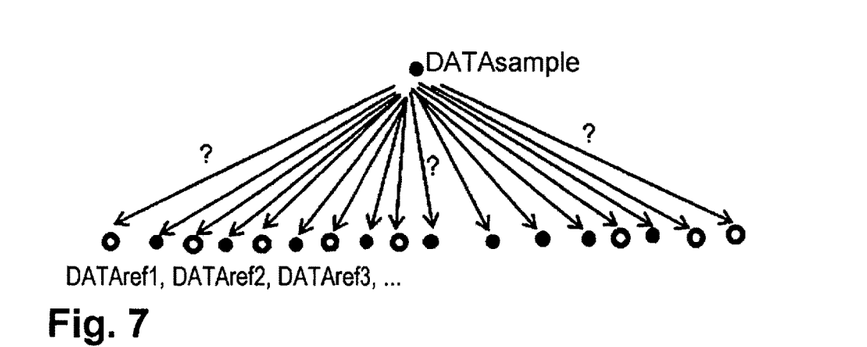
FIGS. 7 to 10 show representations to explain various variants of a comparison between an unknown measurement result with a plurality of known measurement results stored in a database.

FIG. 7 illustrates the performance of the evaluation step "comparison of effect data", wherein DATAsample effect data are inputted into the employed comparison algorithm (see for example step S4 in the above example of embodiment), said DATAsample effect data having been extracted from a measurement curve in the original sense (e.g. the DSCsample' curve in FIG. 2 or the DSCsample curve in FIG. 3).

These unknown DATAsample effect data are then compared with effect data DATAref1, DATAref2, DATAref3, . . . previously stored in the computer unit as datasets. The arrows and question marks ("?") entered by way of example in FIG. 7 are intended to symbolise the comparison or the calculation of the agreement probabilities.

As symbolised in FIG. 7, both effect data based on a measurement (symbolised by "dots") and effect data generated in some other way (symbolised by "circles") can be contained in the database.

Accordingly, features alone (i.e. without an actual measurement curve) can also be stored in the database as unknown "virtual measurement curves" and can be used as reference input variables of the method. This in turn means that the method can also be used as a database search method without an unknown measurement in the original sense. This is illustrated by FIG. 8.

Figure 8:
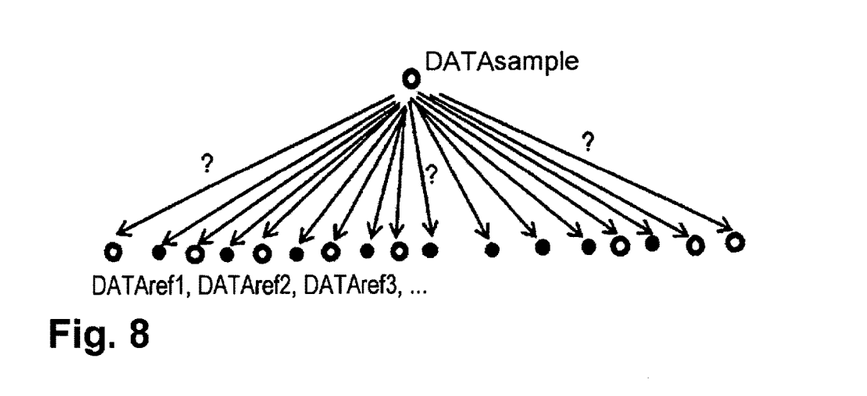

FIG. 8 shows the performance of the evaluation step "comparison of the effect data", wherein DATAsample effect data, which are based on a "virtual measurement curve", are inputted into the employed comparison algorithm.

As already mentioned, the evaluation method can also comprise the step of an assignment of a measurement result (DATAsample effect data) to one of a plurality of previously defined classes of datasets (DATAref1, DATAref2, DATAref3, . . . ). Such an assignment can be carried out on the basis of the result of the calculation of the agreement probabilities. This development is illustrated by FIGS. 9 and 10.

FIG. 9 shows the performance of the evaluation step "comparison of the effect data" similar to that in FIG. 7, a part of the stored datasets DATAref1, DATAref2, DATAref3, . . . being combined however into a given class. In the example represented, there are two classes C1 and C2. In this regard, it should be noted that datasets can simultaneously belong to a plurality of classes, e.g. a material class and at the same time a quality class.

FIG. 10 shows, similar to FIG. 9, a comparison of the DATAsample effect data with previously stored datasets DATAref1, DATAref2, DATAref3, which again are defined in part as belonging to classes C1 and C2, wherein, in contrast with the embodiment according to FIG. 9, the DATAsample effect data are based on a "virtual measurement curve" or literature values of effect data for a known sample.

In this method, the mentioned classes (here for example classes C1 and C2) of the stored measurement curves are groups of measurement curves belonging to a class (e.g. "substance class" of the sample). The user himself can group existing measurement curves (such as DATAref1, DATAref2, DATAref3, . . . ) by suitable user inputs and obtains by the method, for a new measurement curve (such as DSCsample or DATAsample), the given probabilities of belonging to various existing classes.

As a result of the grouping by the user, the method can be increasingly trained in respect of the classification with suitable configuration of the software, without the basic mathematical parameters having to be modified. This has the advantage that the calculation of the agreement probability between different measurement curves can remain independent of the grouping of the measurement curves by the user and the algorithm of the method is therefore robust.

Figure 11:
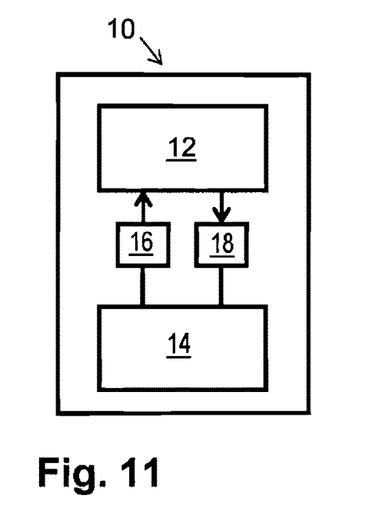
FIG. 11 shows a diagrammatic representation of a system for performing a thermal analysis and an evaluation of measurement results obtained therewith.

FIG. 11 illustrates a system 10 for performing a thermal analysis and a simultaneous or directly following evaluation of measurement results obtained therewith.

System 10 comprises a device 12 for performing a thermal analysis, which can be constituted in a manner known per se, i.e. for example comprising a regulatable temperature-controlled furnace for the temperature control of a sample and a sensor for detecting operational parameters (e.g. furnace temperature) and the measurement signal or signals to be recorded (e.g. DSC signal, sample mass signal, sample length signal etc.).

Furthermore, in the example represented, system 10 comprises a computer unit 14, which controls in a manner known per se the operation (e.g. course of a specific temperature-control program) of thermal analysis device 12 and records the desired measurement signal or signals (in particular, for example, a DCS signal).

For this purpose, computer unit 14 is connected to thermal analysis device 12 via a control interface 16 and a sensor interface 18. In particular, the control of a furnace heating device contained in device 12 can for example take place via (e.g. digital) control interface 16, whereas the measurement signal or signals obtained by means of the sensor device(s) concerned (see for example DCSsample' in FIG. 2) are delivered to computer unit 14 via (e.g. digital) sensor interface 18.

Moreover, an evaluation method of the already described kind is also implemented by means of a computer unit 14 or the software running thereon, so that an evaluation of a measurement result of the thermal analysis obtained by means of thermal analysis device 12 can advantageously be carried out at the same time by means of system 10.

System 10 is also suitable, for example, particularly as a measuring system which is used in quality assurance (including "process control") in a production process (including "processing process" in the narrower sense).

Effects, whose features or similarities between effects or whole measurement curves, such as can be obtained by the rapidly performable evaluation, can serve as quality criteria. Samples investigated by means of system 10 can thus be split up, for example, into various quality classes, e.g. into classes "good parts" and "bad parts".

This can take place, for example, by means of the classification method described by reference to FIGS. 9 and 10, whether it be for example before the actual process (e.g. incoming goods control) or after the actual process (e.g. output control of finished parts or random samples of the same).

For example, additionally detected effects in the measurement curve (compared to known effect data) can indicate impurities of the sample. Additional effects can, moreover, provide information about the previous thermal history or previous thermal treatment of a material, i.e. how the input material in storage or production has been heat-treated. As already mentioned above, a degree of crystallinity or the potential for post-crystallisation (or also for post-crosslinking or post-curing), for example, can also be calculated from the magnitude of an effect (of the "crystallisation peak" or the "crosslinking peak"), which correlates with the mechanical values (hardness, rigidity) of the sample, this often being an important property of the finished part.

On account of the speed of the evaluation method, a further interpretation of the curve recognition (see for example step S5 in the example of embodiment described above) can advantageously be applied in-situ or online in the process.

To save time, it is also possible for example for an ongoing measurement to be terminated prematurely on account of a specific result of the further interpretation of the curve recognition.

The already mentioned "bad parts" of a production process can for example be removed online (controlled by the computer unit concerned).

An entire production process, i.e. machines employed for this, could be stopped or the settings on the machines could be changed online-based on the results of the evaluation, in particular for example the further interpretation of the effect data comparison result.

For example, a tool temperature to be adjusted can be an important influencing parameter on the aforementioned degree of crystallinity of the samples or of the finished parts. That is to say that the tool temperature can be adapted before, during and/or after the performance of the process. Furthermore, a machine for opening and removing a finished part, for example, could be triggered on the basis of the evaluation result. Cycle times in the process can thus be reduced and productivity increased. Finally, raw materials required for production could also be metered in their quantity, i.e. their quantity ratios could be adapted, by using the invention.

Figure 12:
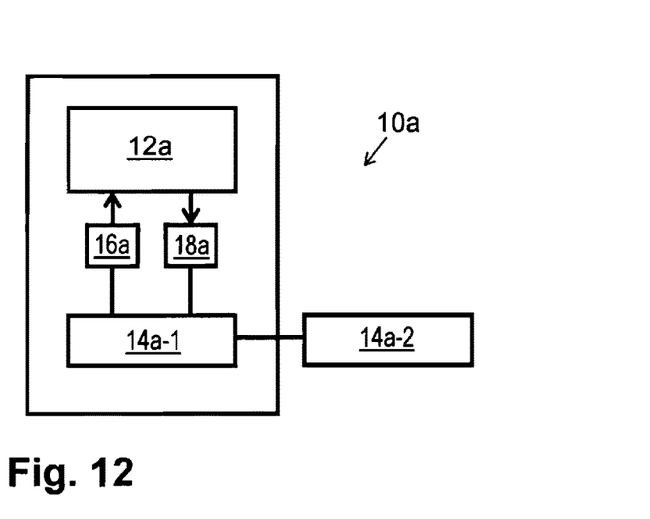
FIG. 12 shows the system from FIG. 11 in a modified embodiment.

FIG. 12 shows a system 10a similar to that from FIG. 11, but in a modified embodiment.

System 10a according to FIG. 12 essentially has the same structure and the same function as system 10 already described according to FIG. 11. In the example of embodiment according to FIG. 12, the same reference numbers are used for identically functioning components, in each case supplemented by a small letter "a" to distinguish the embodiment.

The modification of system 10a consists in the fact that, instead of a computer unit used in common for the thermal analysis control and the analysis evaluation, it comprises two separately implemented computer units 14a-1 and 14a-2.

First computer unit 14a-1 serves in a manner known per se to control the operation (e.g. course of a specific temperature control program) of thermal analysis device 12a and to record the desired measurement signal or signals. Computer unit 14a-1 is structurally combined with device 12a (here: accommodated together with device 12a in a common device housing).

In contrast with this, second computer unit 14a-2 constituted separately therefrom, but being in a communication connection with first computer device 14a-1, serves to carry out the evaluation method of the described type, so that an evaluation of a measurement result obtained by means of thermal analysis device 12a can at the same time be advantageously carried out by means of system 10a.

In the example represented according to FIG. 12, the communication connection between computer units 14a-1 and 14a-2 is implemented by suitable cabling, e.g. by cabling according to a computer network standard.

Figure 13:
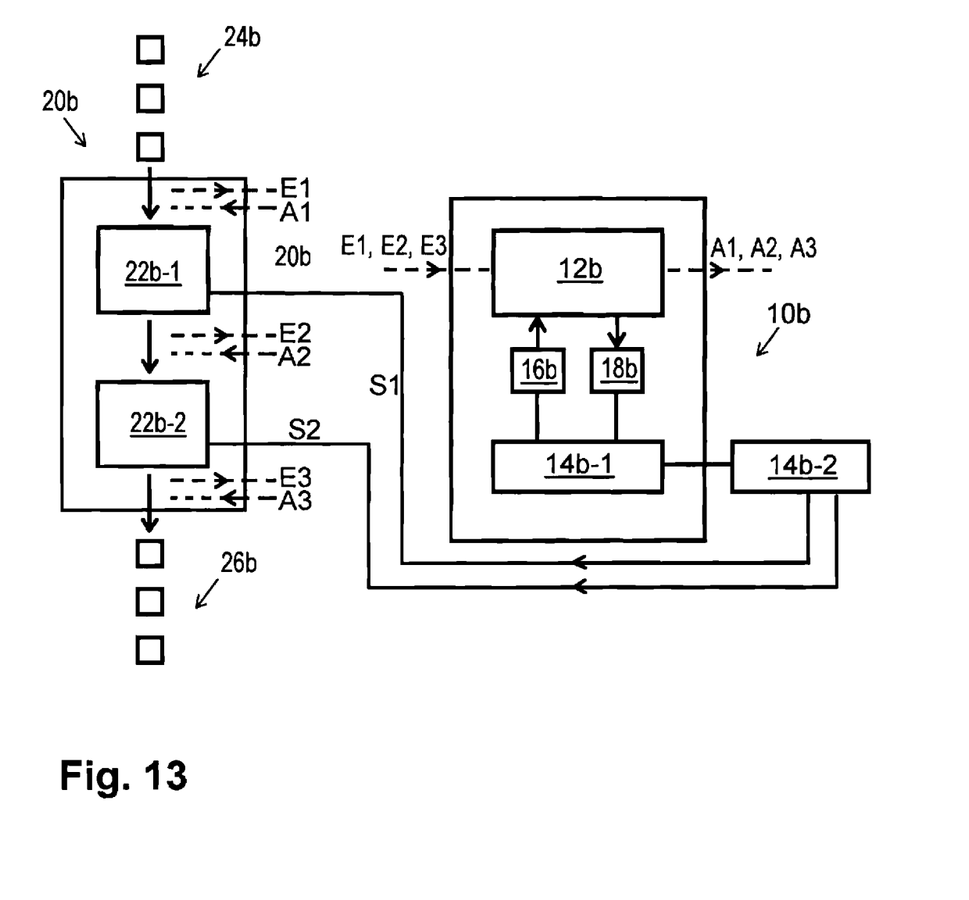
FIG. 13 shows a diagrammatic representation of a system of the design from FIG. 12 in use for quality assurance in an industrial process.

FIG. 13 illustrates an inventive use of system 10b, of the type already described by reference to FIG. 12, for quality assurance in an industrial process. System 10b accordingly comprises a thermal analysis device 12b, a computer arrangement with communicating computer units 14b-1 and 14b-2, a sensor interface 18b and a control interface 16b.

In the case of the system use or quality assurance according to FIG. 13, an (e.g. industrial) production or processing plant 20b is provided, to which "raw products" or initial materials 24b are fed and which produces "end products" 26b therefrom.

For this purpose, plant 20b comprises two processing stations (machines) 22b-1 and 22b-2 in the represented example. These stations 22b-1, 22b-2, passed through successively, thus form a production and processing path for the production of end products 26b.

In the example represented, products are removed from their conveyance along the production and processing path at least on a random sample basis at three points (see dashed arrow at E1, E2 and E3) for the performance of the quality assurance, are subjected to the thermal analysis by means of thermal analysis device 12b and are transferred back into the processing path at the same point in each case (A1, A2 and A3 respectively).

As already described for the preceding example from FIG. 12, an evaluation of the respective measurement result is carried out by means of computer unit 14b-2.

Depending on the results of these analyses, an intervention into the production and processing process takes place as required and automatically (initiated by computer unit 14b-2). For this purpose, the communication or operative connections represented in FIG. 13 by S1 and S2 are provided, which permit control signals to be transmitted to change the operating mode (e.g. adaptation of the operational parameters) of stations 22b-1 and 22b-2 employed in the process. Alternatively or in addition, alerting of operating personnel can for example also take place in such a case.

To sum up, the invention provides in particular an advantageous method for the automatic recognition and classification of measurement curves in the area of thermal analysis as well as the application of such a method in processes, e.g. industrial processes of quality assurance or production.

What is claimed is:

1. A method for evaluating a measurement result of a thermal analysis, comprising the step of:
   calculating, via a program controlled computer unit, a plurality of probabilities of an agreement of the measurement result with a plurality of datasets previously stored in the computer unit in order to identify at least one probability of the plurality of probabilities,
   wherein the calculation is based on a comparison of effect data previously extracted from a measurement curve of the thermal analysis with corresponding stored effect data of the dataset.

2. The method according to claim 1, wherein the effect data comprises at least minima, maxima and steps in the course of the measurement curve.

3. The method according to claim 1, wherein the effect data for each effect are represented as a given feature vector, the feature vector having vector components which represent quantitatively specific properties of the effect concerned.

4. The method according to claim 1, further comprising the step of extracting the effect data from the measurement curve of the thermal analysis using the computer unit.

5. The method according to claim 4, further comprising the step of processing the measurement curve using the computer unit before extracting the effect data from the measurement curve.

6. The method according to claim 1, further comprising the step of assigning the measurement result to the at least one dataset using the computer unit, wherein the assignment is based on a result of the calculation of one or more agreement probabilities.

7. Use of a method for evaluating a measurement result of a thermal analysis, the use of the method in an area of quality assurance in production or processing of goods, comprising the steps of:
   performing a thermal analysis on produced or processed goods at least on a random sample basis,
   evaluating the measurement result of the thermal analysis by means of a method that includes calculating, via a program controlled computer unit, at least one probability of an agreement of the measurement result with at least one dataset previously stored in the computer unit, wherein the calculation is based on a comparison of effect data previously extracted from a measurement curve of the thermal analysis with corresponding stored effect data of the dataset,
   wherein an assignment of a given measurement result takes place to one of a plurality of quality classes and/or an interpretation of the given measurement result takes place.

8. A computer unit integrated into or connected to a device for performing a thermal analysis, the computer unit having instructions executing on computer readable medium for:
   calculating, via a program controlled computer unit, at least one probability of an agreement of the measurement result with at least one dataset previously stored in the computer unit,
   wherein the calculation is based on a comparison of effect data previously extracted from a measurement curve of the thermal analysis with corresponding stored effect data of the dataset.

9. A computer program product containing instructions for automated performance of a thermal analysis by means of a processing system, the computer program product executing on the processing system for:

calculating, via a program controlled computer unit, at least one probability of an agreement of the measurement result with at least one dataset previously stored in the computer unit,     wherein the calculation is based on a comparison of effect data previously extracted from a measurement curve of the thermal analysis with corresponding stored effect data of the dataset.

10. A system, comprising:

a device performing a thermal analysis, and a computer unit configured to evaluate a measurement result of the thermal analysis by calculating at least one probability of an agreement of the measurement result with at least one dataset previously stored in the computer unit,     wherein the calculation is based on a comparison of effect data previously extracted from a measurement curve of the thermal analysis with corresponding stored effect data of the dataset.

11. The method according to claim 2, wherein the effect data further comprises maxima, minima and steps in the course of a derivative of the course of the measurement curve.

12. The method according to claim 1, wherein the plurality of probabilities comprises a probability for each of the plurality of datasets, each probability representing similarities or differences.

13. The method according to claim 1, wherein the plurality of datasets comprises more than twenty datasets.

14. The method according to claim 1, wherein the at least one probability identifies a material class for a substance.

15. The method according to claim 1, wherein the at least one probability identifies a quality class for a substance.

16. The method according to claim 5, wherein the step of processing comprises at least one of the following:

smoothing;

filtering;

eliminating a region;

subtracting an empty curve.

17. The method according to claim 1, wherein extraction of effect data from the measurement curve comprises segmentation of the measurement curve, where the measurement curve is split up into regions for further evaluation.

\* \* \* \* \*